United States Patent
Fujii et al.

(10) Patent No.: US 11,439,848 B2
(45) Date of Patent: Sep. 13, 2022

(54) RADIATION IRRADIATING SYSTEM AND MOVING OBJECT TRACKING SYSTEM

(71) Applicants: HITACHI, LTD., Tokyo (JP); NATIONAL UNIVERSITY CORPORATION HOKKAIDO UNIVERSITY, Sapporo (JP)

(72) Inventors: Yusuke Fujii, Sapporo (JP); Naoki Miyamoto, Sapporo (JP); Kikuo Umegaki, Sapporo (JP); Shinichi Shimizu, Sapporo (JP); Toru Umekawa, Tokyo (JP); Takahiro Yamada, Tokyo (JP)

(73) Assignees: HITACHI, LTD., Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 508 days.

(21) Appl. No.: 16/302,106

(22) PCT Filed: May 11, 2017

(86) PCT No.: PCT/JP2017/017950
§ 371 (c)(1),
(2) Date: Nov. 16, 2018

(87) PCT Pub. No.: WO2017/203998
PCT Pub. Date: Nov. 30, 2017

(65) Prior Publication Data
US 2019/0143146 A1 May 16, 2019

(30) Foreign Application Priority Data
May 24, 2016 (JP) .............................. JP2016-103596

(51) Int. Cl.
*A61N 5/10* (2006.01)
*A61B 6/02* (2006.01)
*A61B 90/00* (2016.01)

(52) U.S. Cl.
CPC ............ *A61N 5/1067* (2013.01); *A61B 6/022* (2013.01); *A61N 5/10* (2013.01); *A61N 5/107* (2013.01);
(Continued)

(58) Field of Classification Search
CPC ........ A61N 5/1067; A61N 5/107; A61N 5/10; A61N 5/1081; A61N 2005/1061;
(Continued)

(56) References Cited

U.S. PATENT DOCUMENTS 6,307,914 B1 10/2001 Kunieda et al.
2014/0018604 A1 1/2014 Ishikawa et al.
(Continued)

FOREIGN PATENT DOCUMENTS

| EP | 2 835 150 A1 | 2/2015 |
|---|---|---|
| JP | 3053389 B | 6/2000 |
| JP | 2015-029793 A | 2/2015 |

OTHER PUBLICATIONS

International Search Report of PCT/JP2017/017950 dated Jul. 18, 2017.
(Continued)

*Primary Examiner* — Christopher Koharski
*Assistant Examiner* — Remy C Cooper
(74) *Attorney, Agent, or Firm* — Mattingly & Malur, PC

(57) ABSTRACT

A template matching is performed on two fluoroscopic images by using a template image prepared in advance and a position corresponding to a high matching score is listed as a candidate for the position of a marker 29. From two lists of the candidates of the position of the marker 29, the lengths
(Continued)

of common vertical lines for all combinations are calculated. Then, the position of the marker 29 is detected based on the matching score and the common vertical line. Then, based on the detected position of the marker 29, an amount of a proton beam to be irradiated to a target is controlled. Therefore, a tracking target can be accurately detected even when the conditions for X-ray fluoroscopy is severe, e.g., a thick object.

10 Claims, 6 Drawing Sheets

(52) U.S. Cl.
CPC ...... *A61N 5/1081* (2013.01); *A61B 2090/376* (2016.02); *A61B 2090/3966* (2016.02); *A61N 2005/1061* (2013.01); *A61N 2005/1074* (2013.01); *A61N 2005/1087* (2013.01)

(58) Field of Classification Search
CPC .... A61N 2005/1074; A61N 2005/1087; A61N 5/1049; A61B 6/022; A61B 2090/376; A61B 2090/3966
See application file for complete search history.

(56) References Cited

U.S. PATENT DOCUMENTS

| 2015/0065779 A1* | 3/2015 | Suzuki | A61N 5/1039 600/1 |
| 2015/0094516 A1 | 4/2015 | Taguchi et al. | |

OTHER PUBLICATIONS

Extended European Search Report received in corresponding European Application No. 17802592.0 dated Nov. 12, 2019.

* cited by examiner

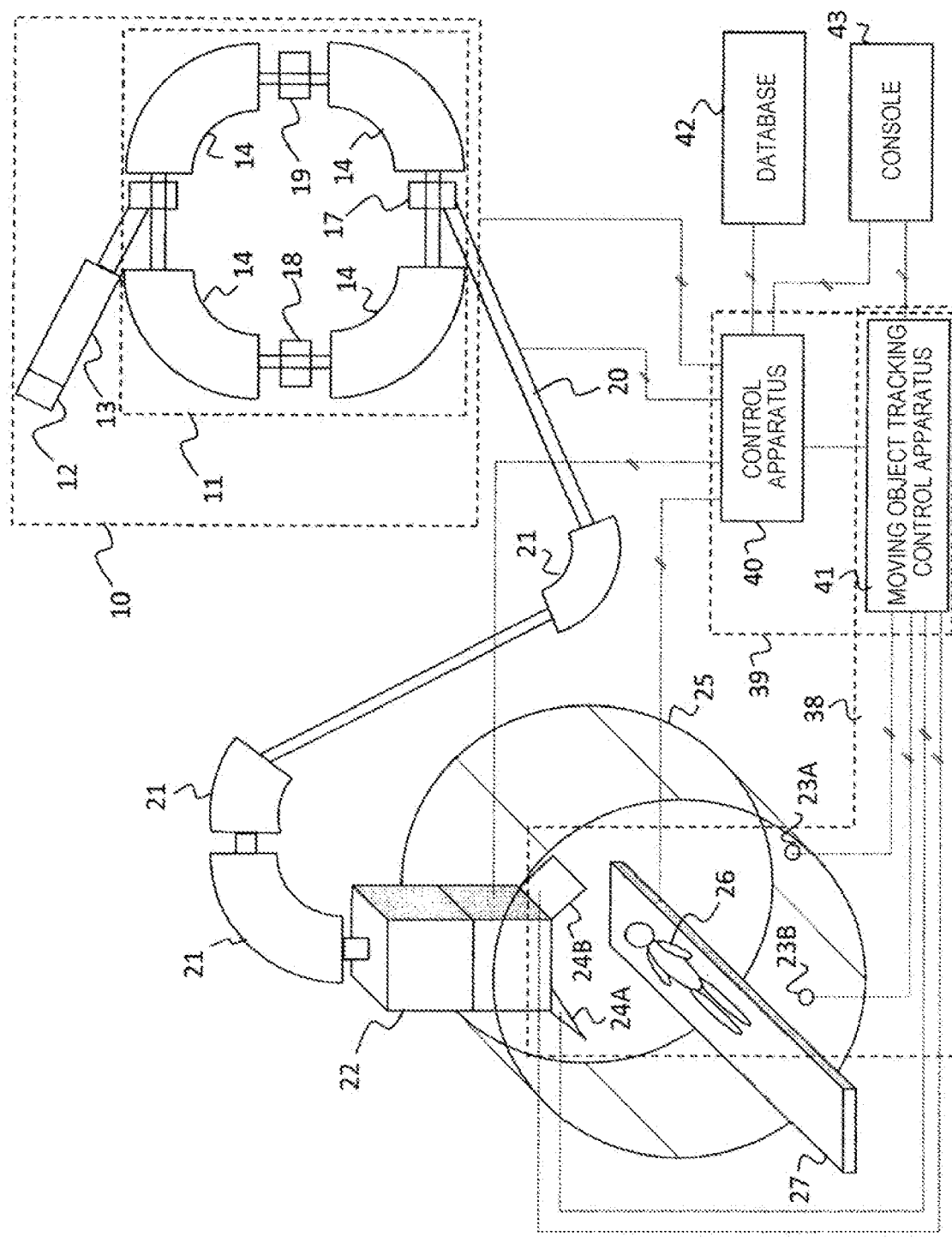
[FIG. 1]

[FIG. 2]
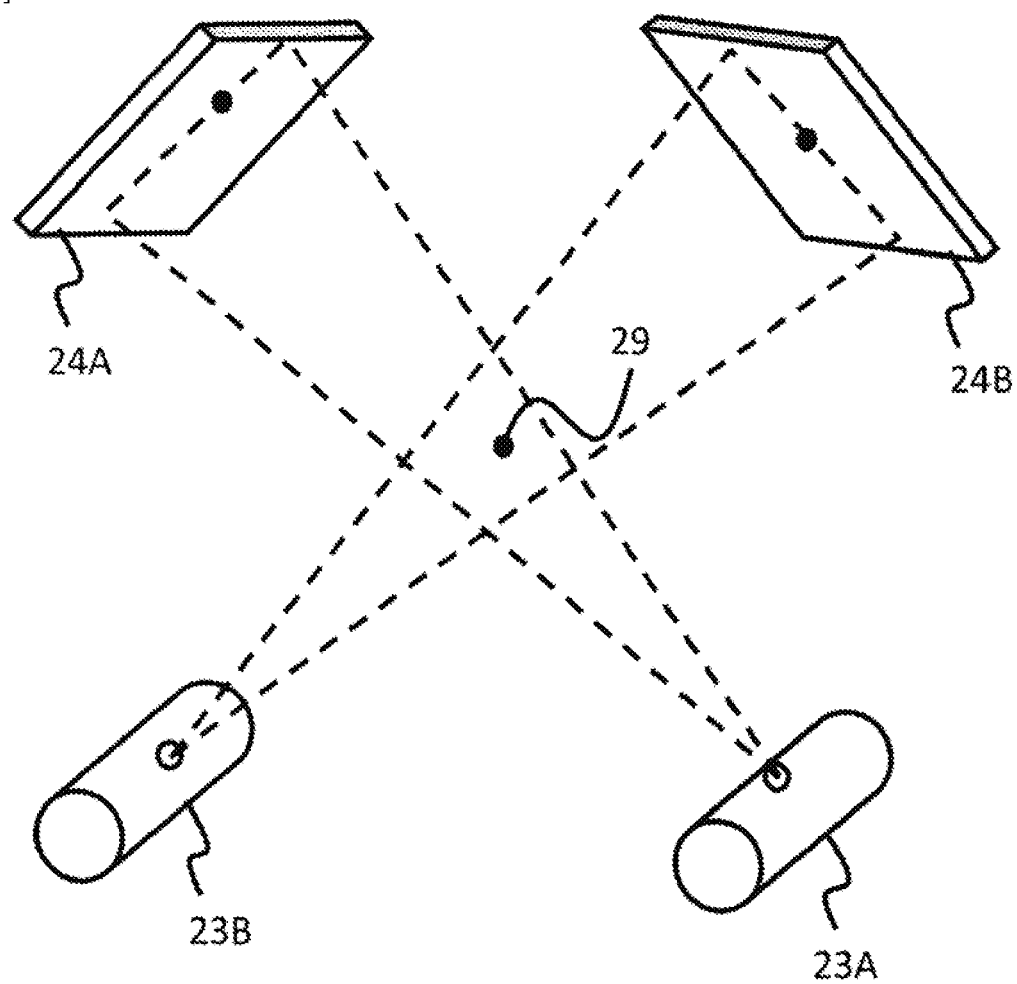

[FIG. 3]
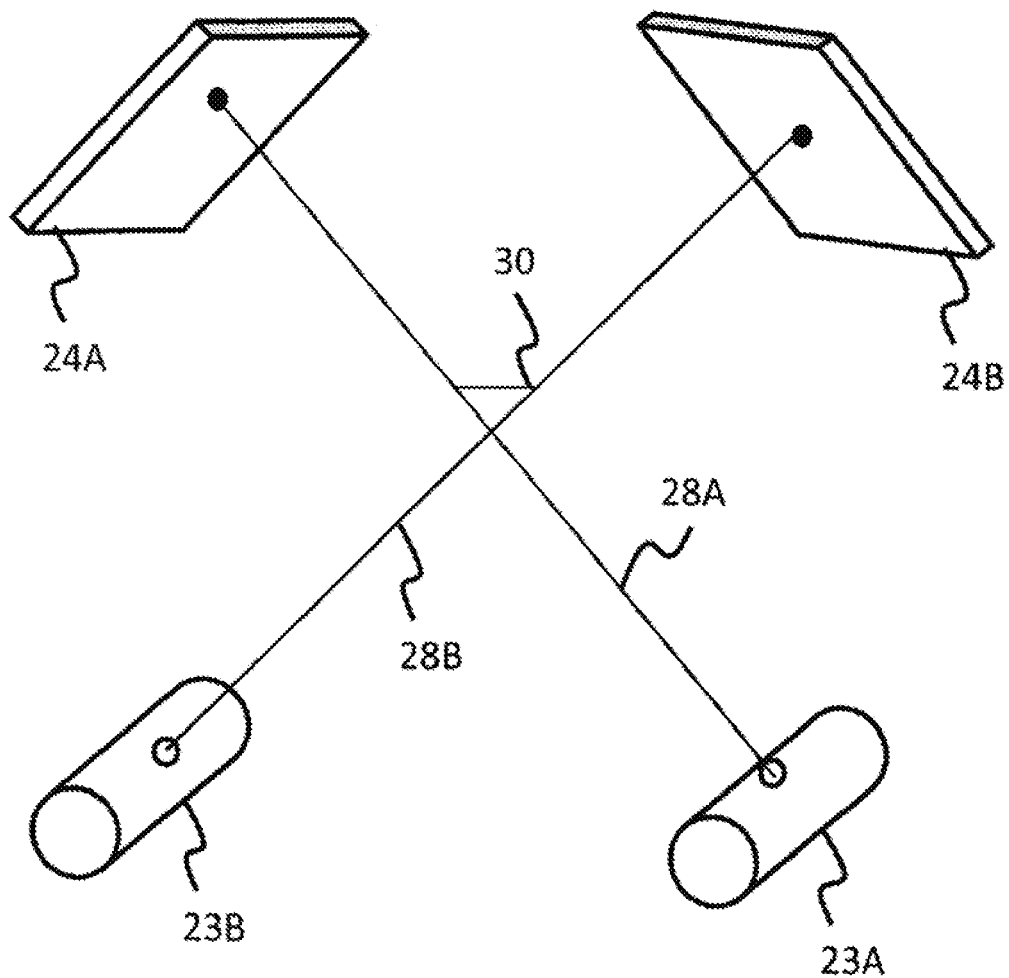
[FIG. 4]
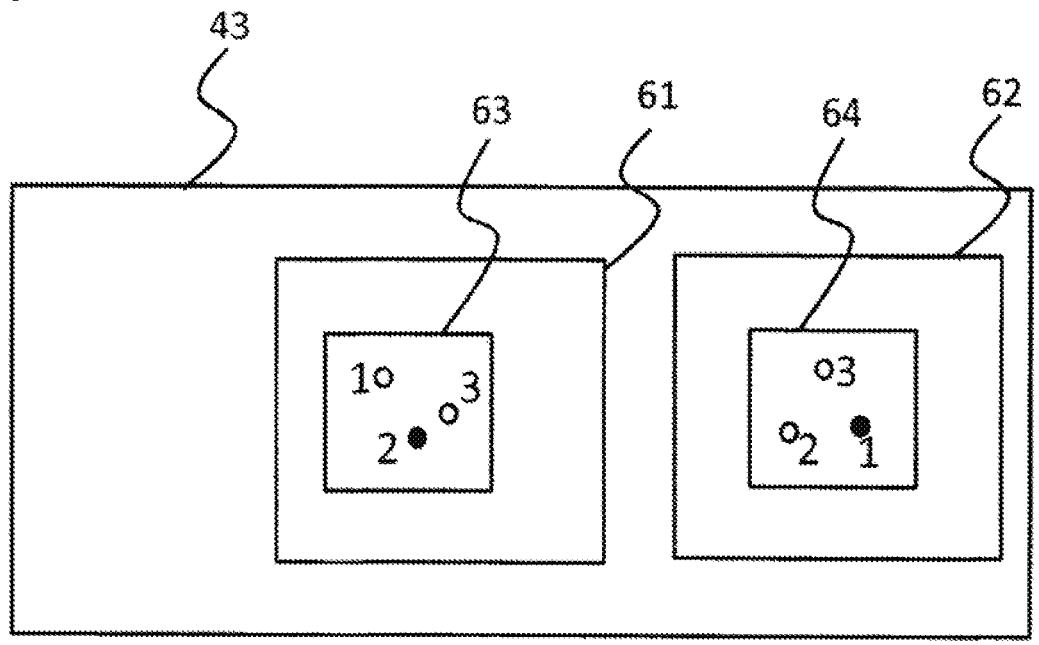

[FIG. 5A]

| CANDIDATE NUMBER | SCORE $S_A$ |
|---|---|
| 1 | 80 |
| 2 | 70 |
| 3 | 50 |

[FIG. 5B]

| CANDIDATE NUMBER | SCORE $S_a$ |
|---|---|
| 1 | 80 |
| 2 | 50 |
| 3 | 60 |

[FIG. 6]

| A CANDIDATE NUMBER | B CANDIDATE NUMBER | LENGTH OF COMMON VERTICAL LINE, L | EVALUATION FUNCTION F |
|---|---|---|---|
| 1 | 1 | 2.5 | 164 |
| 1 | 2 | 1.8 | 135 |
| 1 | 3 | 1.6 | 146 |
| 2 | 1 | 0.1 | 250 |
| 2 | 2 | 2.2 | 124 |
| ⋮ | ⋮ | ⋮ | ⋮ |

[FIG. 7A]
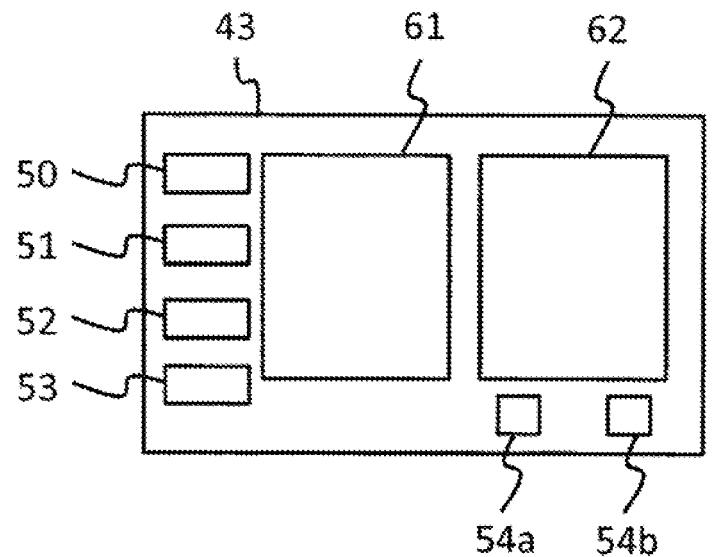
[FIG. 7B]
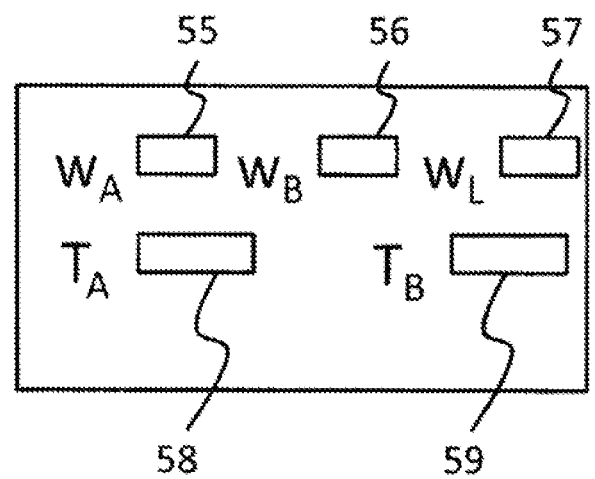

[FIG. 8]
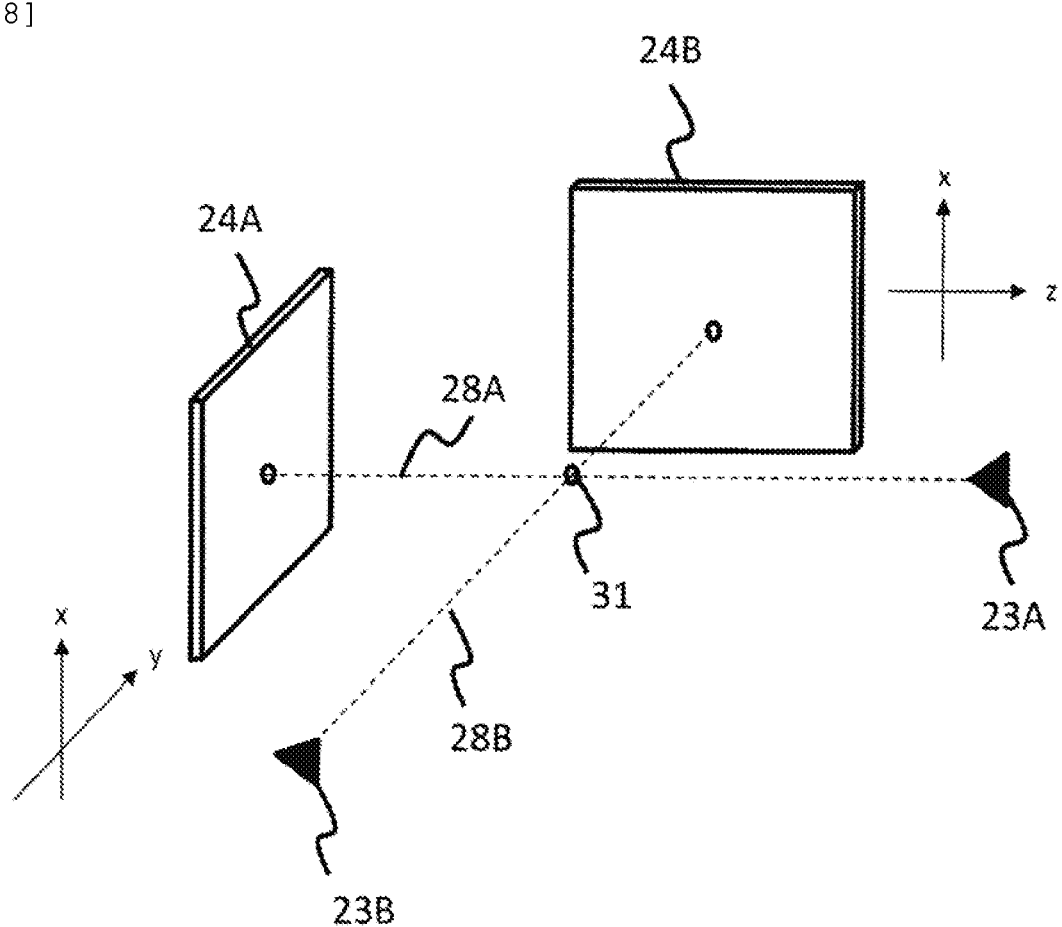

ization system for curing a target volume, such as tumor, by
irradiating a radiation, such as a charged particle beam or an
X-ray, thereto and a moving object tracking system suitable
for such a radiation irradiating system.

BACKGROUND ART

As an example of a moving object tracking irradiating
apparatus capable of automatically calculating the position
of a tumor moving around in a body in real time and
ensuring substantially necessary accuracy without depending on the absolute accuracy of a machine system, PTL 1
discloses a moving object tracking irradiating apparatus
including a fluoroscopic device that simultaneously images
tumor marker embedded in the vicinity of a tumor in first
and second directions to obtain first and second fluoroscopic
images; an image input recognition processor for executing
a template matching according to the gray-level normalized
cross-correlation method applied to the a template image of
tumor markers registered in advance on the digitized first
and second fluoroscopic images at a predetermined frame
rate in real time and calculates first and second 2-dimensional coordinates of the tumor markers based on first and
second fluoroscopic transformation matrices, a central processing unit for calculating 3-dimensional coordinates of the
tumor markers based on the first and second 2-dimensional
coordinates, and an irradiation control unit that controls
irradiation of a medical irradiation of a linac based on the
calculated 3-dimensional coordinates of the tumor markers.

CITATION LIST

Patent Literature

PTL 1: Japanese Patent No. 3053389

SUMMARY OF INVENTION

Technical Problem

A method like irradiation of a radiation, such as a charged
particle beam or an X-ray, to patients having a disease like
a cancer is known. The charged particle beam includes a
proton beam, a carbon beam, etc. A radiation irradiating
system used for such an irradiation forms a dose distribution
suitable for the shape of a target, such as a tumor, in the body
of a patient fixed on a patient bed called a couch.

Incidentally, when a target, such as tumor, is moved by
respiration or the like, an accurate irradiation becomes
difficult. Therefore, it has been realized in recent years to
perform a gate irradiation for irradiating a radiation only
when a target is within a predetermined range (gate range).

In PTL 1, a method called a moving object tracking
irradiation in which gate irradiation is performed based on
the position of a marker embedded in the vicinity of a target
volume is disclosed.

A marker used for a gate irradiation as disclosed in PTL
1 is a metal sphere having a diameter of about 2 mm, for
example.

In the moving object tracking irradiation, a gate irradiation is performed based on the position of a tracking target,
such as a marker embedded in the vicinity of the target
volume, or an irradiation target itself. The position of a
tracking target, such as a marker, is measured by using X-ray
fluoroscopic images in two intersecting directions. The
position of a tracking target in a fluoroscopic image is
detected by a method called a template matching.

The template matching is a method of comparing an
image of a tracking target prepared in advance called a
template image with a fluoroscopic image of the tracking
target and detecting a pattern closest to the template image
in the fluoroscopic image. A position at which two lines
connecting a position on an X-ray measuring instrument at
which a tracking target is captured and fluoroscopic X-ray
generators are closest are regarded as the position of the
tracking target. A vertical line can be drawn with respect to
the two lines at a position where the two lines are closest to
each other. The line is referred to as a common vertical line,
and the midpoint of the common vertical line is regarded as
the position of the tracking target.

In the technique disclosed in PTL 1, tracking targets are
independently detected on two fluoroscopic images. Therefore, if an X-ray fluoroscopic condition is severe (e.g., a
target object is thick), if a structure similar to the tracking
object appears in the vicinity of the tracking target on the
fluoroscopic image, an object that is not the tracking target
can be erroneously detected as the tracking target. The
erroneous detection of the tracking target appears as the
length of the common vertical line increases. If the tracking
target is erroneously detected, since the two lines connecting
the positions on the X-ray measuring instrument at which
the tracking target is imaged and fluoroscopy X-ray generators are separated from each other, and thus the length of the
common vertical line increases.

When an erroneous detection of a tracking target occurs,
it is necessary to stop irradiation of a radiation for forming
a distribution and manually operate a device to re-detect a
correct tracking target, and thus the irradiation time
increases.

The present invention is to provide a radiation irradiating
system and a moving object tracking system capable of
accurately detecting a tracking target even when an X-ray
fluoroscopic condition is severe (e.g., a target object is
thick).

Solution to Problem

In order to solve the above problem, for example, the
configurations described in the claims are employed. The
present invention includes a plurality of means for solving
the above-mentioned problems, for example, a radiation
irradiating system including: a radiation irradiating device
configured to generate a radiation; two or more pairs of
X-ray fluoroscopic devices configured to capture fluoroscopic images of a tracking target, wherein each pair
includes one X-ray measuring device and one X-ray generator; and a control unit configured to control the radiation
irradiating device and detect a position of the tracking target
from the fluoroscopic images captured by the X-ray fluoroscopic devices, wherein the control unit calculates values
indicating the accuracy of detection of candidates of a
position of the tracking target and a value representing a
correlation between the positions of the candidates from the
fluoroscopic images acquired by the two or more X-ray
fluoroscopic devices, detects the position of the tracking
target based on the value representing the accuracy of the
detection and the value representing the correlation, and control the radiation to be irradiated onto the target based on the detected position of the tracking target.

Advantageous Effects of Invention

According to the present invention, even when an X-ray fluoroscopic condition is sever (e.g., a target object is thick), a tracking target can be accurately detected, and the irradiation time can be shortened, for example.

BRIEF DESCRIPTION OF DRAWINGS

FIG. 1 is an overall configuration diagram of a proton beam irradiating system according to an embodiment of the present invention.

FIG. 2 is a schematic diagram showing that a moving object tracking system of the present embodiment obtains a fluoroscopic image.

FIG. 3 is a schematic diagram showing that a moving object tracking system according to the present embodiment calculates a marker position from a fluoroscopic image.

FIG. 4 is a diagram showing an example of a process for searching for a marker from a fluoroscopic image according to the present embodiment.

FIG. 5A is a diagram showing an example of matching score values at candidate positions of each marker in FIG. 4.

FIG. 5B is a diagram showing an example of matching score values at candidate positions of each marker in FIG. 4.

FIG. 6 is a diagram showing an example of a calculation result of an evaluation function in the present embodiment.

FIG. 7A is a schematic diagram showing an example of a console screen in the present embodiment.

FIG. 7B is a schematic diagram showing another example of a console screen in the present embodiment.

FIG. 8 is a schematic diagram showing another example that a moving object tracking system according to the present embodiment calculates a marker position from a fluoroscopic image.

DESCRIPTION OF EMBODIMENTS

Embodiments of a radiation irradiating system and a moving object tracking system of the present invention will be described with reference to FIGS. 1 to 8.

The present invention provides an X-ray irradiating system or a proton beam irradiating system, e.g., a radiation irradiating system like a heavy particle beam irradiating system for irradiating heavy particles (e.g., carbon, etc.) onto a target. In the present embodiment proton, descriptions will be given by using a proton beam irradiating system using protons as a radiation to irradiate as an example.

FIG. 1 is an overall configuration diagram of a proton beam irradiating system according to the present embodiment.

In FIG. 1, the proton beam irradiating system includes a proton beam generator (radiation generator) 10, a beam transport line 20, an irradiation nozzle 22, a moving object tracking system 38, a couch 27, a control apparatus 40, etc.

The proton beam generator 10 includes an ion source 12, a linac 13, and a synchrotron 11. The synchrotron includes a bending magnet 14, a quadrupole electromagnet (not shown), a radiofrequency acceleration system 18, a radiofrequency extractor 19, an extraction deflector 17, etc. The ion source 12 is connected to the linac 13, and the linac 13 is connected to the synchrotron 11. In the proton beam generator 10, a proton beam generated from the ion source 12 is accelerated forward by the linac 13 and is incident on the synchrotron 11. The proton beam further accelerated by the synchrotron 11 is emitted to beam transport line 20.

The beam transport line 20 is provided with a plurality of bending magnets 21 and quadrupole electromagnets (not shown) and is connected to the synchrotron 11 and the irradiation nozzle 22. Also, a portion of the beam transport line 20 and the irradiation nozzle 22 are installed in a tubular gantry 25 and can rotate together with the gantry 25. The proton beam emitted from the synchrotron 11 converges by the quadrupole electromagnet while passing through the beam transport line 20, is bent by the bending magnets 21, and is incident on the irradiation nozzle 22.

The irradiation nozzle 22 includes two pairs of scanning magnets, a dose monitor, and a position monitor (none of which are shown). The two pairs of scanning magnets are installed in mutually orthogonal directions and a proton beams can be bent, such that the proton beam reaches a desired position in a plane vertical to a beam axis at the position of a target. The dose monitor measures an amount of an irradiated proton beam. The position monitor can detect positions through which the proton beam has passed. The proton beam passing through the irradiation nozzle 22 reaches a target in an irradiation target 26. Incidentally, in case of treating a patient having a cancer, for example, the irradiation target 26 represents a patient, and the target represents a tumor or the like.

A bed on which the irradiation target 26 is placed is referred to as the couch 27. Based on an instruction from the control apparatus 40, the couch 27 can move in directions along three orthogonal axes and can further rotate around each of the axes. With these movements and rotations, the position of the irradiation target 26 can be moved to a desired position.

The control apparatus 40 is connected to the proton beam generator 10, the beam transport line 20, the irradiation nozzle 22, a moving object tracking control apparatus 41, the couch 27, a database 42, a console 43, etc., and controls these devices.

The moving object tracking system 38 includes an X-ray fluoroscopic device, which includes two fluoroscopic X-ray generators 23A and 23B and two X-ray measurement devices 24A and 24B, and the moving object tracking control apparatus 41.

A pair of the fluoroscopic X-ray generators 23A and the X-ray measuring device 24A and a pair of the fluoroscopic X-ray generating device 23B and the X-ray measuring device 24B are installed, such that paths of their X-rays intersect each other. Also, it is preferable that the two pairs of fluoroscopic X-ray generators 23A and 23B and the X-ray measuring devices 24A and 24B are installed in directions orthogonal to each other, but they do need to be orthogonal to each other. In addition, the fluoroscopic X-ray generators 23A and 23B and the X-ray measuring devices 24A and 24B do not necessarily need to be arranged inside the gantry 25 and may be disposed at fixed positions, such as a ceiling and a floor.

The moving object tracking control apparatus 41 calculates the position of a marker 29 on the basis of a signal input from the X-ray fluoroscopic device, determines whether to permit extraction of a proton beam on the basis of the position of the marker 29, and transmits a signal indicating whether to irradiate a proton beam to the control apparatus 40. A control unit consists of the moving object tracking control apparatus 41 and the above-mentioned control apparatus 40.

More specifically, as shown in FIG. 2, when the marker 29 is imaged with X-rays generated from the two fluoroscopic X-ray generators 23A and 23B, the marker is projected onto the respective X-ray measuring devices 24A and 24B. The moving object tracking control apparatus 41 calculates the 3-dimensional position of the marker 29 embedded in the irradiation target 26 from two acquired fluoroscopic images and, based on a result thereof, determines whether to permit extraction of a proton beam based on the position of the marker 29. For example, it is determined whether the position of the target acquired from the position of the marker 29 is within a predetermined gate range (irradiation permissible range). If it is determined that the position of the target is within the gate range, a gate ON signal is transmitted to the control apparatus 40. On the other hand, when it is determined that the position of the target is not within the gate range, a gate OFF signal is transmitted and extraction is not permitted.

Acquisition of a fluoroscopic image by the X-ray fluoroscopic apparatus is performed at a regular interval of 30 Hz, for example. An acquired fluoroscopic image shows the marker 29 embedded in a body and specifies the position of the marker 29 within the irradiation target 26 through a template matching with a template image of the marker 29 prepared in advance. Since it takes time to search for the entire range of a fluoroscopic image, the position of the marker 29 is searched for only within the range of a predetermined size centered at the position of the marker 29 in a previous fluoroscopic image.

FIG. 3 shows two lines connecting positions of the marker 29 on the X-ray measuring devices 24A and 24B detected through a template matching and the fluoroscopic X-ray generators 23A and 23B. Ideally, these two lines intersect each other at one point and the point of the intersection is where the marker 29 exists.

However, in practice, two lines do not intersect each other and are in a twisted relationship due to errors in accuracy of a template matching and installation of an X-ray fluoroscopic device. A common vertical line can be drawn to a position where the two lines in the twisted relation are closest to each other. The common vertical line is referred to as a common vertical line 30. Then, the middle point of the common perpendicular is set as the position of the marker 29.

Here, when the marker 29 is not correctly detected on at least one of the fluoroscopic images, the length of a common vertical line increases. Using the phenomenon, if the length of the common vertical line 30 exceeds a preset threshold value, it is determined that the possibility of an incorrect detection of the marker 29 is high. Therefore, in this case, even if the position of the marker 29 is within the gate range, the moving object tracking control apparatus 41 transmits a gate OFF signal to the control apparatus 40 and stop the irradiation of a proton beam.

The technical feature of the moving object tracking control apparatus 41 of the present embodiment relates to a method of detecting the marker 29. In a template matching, a fluoroscopic image is compared with a template image of the marker 29 prepared in advance to calculate a degree of consistency with the template image, which is referred to as a matching score. The higher the matching score is, the more consistent that the fluoroscopic image being searched for is with the template image.

As a method of detecting the position of a marker, there is, for example, a method of detecting a position corresponding to the highest matching score within a search range as the position of the marker 29.

On the other hand, in the moving object tracking control apparatus 41 of the present embodiment, one or more candidates for the position of the marker 29 are detected from the respective fluoroscopic images acquired by the X-ray measuring devices 24A and 24B and values representing the accuracy of the detection of the candidates are calculated. Furthermore, a value representing the correlation between the candidates of the position of the marker 29 detected by the respective X-ray measuring devices 24A and 24B is calculated. Thereafter, the position of the marker 29 is detected based on the values representing the accuracy of the detection and the value representing the correlation. Then, based on the detected position of the marker 29, by outputting a signal to the control apparatus 40, a proton beam to be irradiated onto the target in the irradiation target 26 is controlled.

Here, the values indicating the accuracy of the detection are set as a matching score in the template matching for the fluoroscopic image acquired by the X-ray measuring device 24A and a matching score in the template matching for the fluoroscopic image acquired by the X-ray measuring device 24B. Also, the length of a common vertical line corresponding to the shortest distance between two lines connecting positions on the X-ray measuring device 24A corresponding to the positions of candidates of the marker 29 in the fluoroscopic image acquired by the X-ray measuring device 24A and the X-ray generator 23A and positions on the X-ray measuring device 24B corresponding to the positions of candidates of the marker 29 in the fluoroscopic image acquired by the X-ray measuring device 24B and the X-ray generator 23B is used as a value representing the correlation of the positions of the marker 29.

In addition, the moving object tracking control apparatus 41 is configured to apply weight to the matching scores, which are values indicating the accuracy of the detection, or the common vertical line and detect the position of the marker 29 based on a result of the weight application.

More specifically, the minimum matching score $T_A$ of the fluoroscopic image A61 and the minimum matching score $T_B$ of the fluoroscopic image B62 are set in advance as the minimum values of matching scores from the console 43. This specification will be described below in detail. FIG. 4 shows a fluoroscopic image A61 acquired by the X-ray measuring device 24A and a fluoroscopic image B62 acquired by the X-ray measuring device 24B. There are a search range A63 and a search range B64 in the respect fluoroscopic images. FIG. 4 shows a case where there are three positions in each search range where matching scores exceed a predetermined minimum matching score $T_A$ and $T_B$. In FIG. 4, the black circles represent the projected image of the actual marker 29.

Next, the moving object tracking control apparatus 41 lists the positions of the candidates of the marker 29 that exceeds the minimum matching scores $T_A$ and $T_B$ for each of the fluoroscopic image A61 and the fluoroscopic image B62.

Here, when there is a group that are determined to be selected for a same candidate selected from candidates selected as candidates of the marker 29 in the list created by each of the fluoroscopic image A 61 and the fluoroscopic image B 62, the candidate with the highest matching score is treated as the position of the marker 29 candidate in that group and the other candidates in the group are deleted from the list. For example, when there are proximity candidates closer to the size of the marker 29, the candidate with the highest score among such candidates is saved and the other candidates are deleted from the list. In this regard, a range serving as a reference for determining that the same candidate for deleting the proximity candidates is selected is set from the console 43 in advance. FIG. 5 shows a list of candidates for the marker 29 after deletion.

Next, the moving object tracking control apparatus 41 calculates the lengths of common vertical lines for all combinations of candidates in the lists regarding the fluoroscopic images A61 and B62. A list of the combinations is shown in FIG. 6. Two matching scores and the length of the common perpendicular are acquired per combination, and the marker 29 is detected based on these three parameters. The evaluation function $F=W_A \times S_A + W_B \times S_B + W_L \times (1/L)$ is calculated when the score for a fluoroscopic image A is $S_A$, the score for a fluoroscopic image B is $S_B$, and the length of the common perpendicular is L. Here, $W_A$, $W_B$, and $W_L$ are weights of respective terms. These weights can be set while watching the console 43 from a screen image as shown in FIG. 7B to be described later.

Next, the moving object tracking control apparatus 41 selects a combination corresponding to the largest F from among all combinations and detects the midpoint of the corresponding common vertical line as the position of the marker 29. Then, if the detected position is within a preset gate range, the moving object tracking control apparatus 41 transmits a gate ON signal to the control apparatus 40 to permit irradiation of a proton beam. If the detected position is outside the gate range, the moving object tracking control apparatus 41 transmits a gate OFF signal to the control apparatus 40 to not to allow irradiation of a proton beam.

The moving object tracking control apparatus 41 compares a matching score in a template matching regarding the fluoroscopic image A61 or a matching score in a template matching regarding the fluoroscopic image B62 in the combination selected as the position of the marker 29 with a first predetermined value set in advance and outputs a result thereof to the console 43. Here, the comparison may be made with respect to the number of candidates for the position of the marker 29 or the number of the candidates may be compared with a predetermined value and a result thereof may be output to the console 43.

In the examples shown in FIGS. 4 to 6, if a determination is made only based on matching scores, first candidates (first candidate of each of) the fluoroscopic image A61 and the fluoroscopic image B62 corresponding to the highest matching scores are selected. In this case, a detection error occurs in the fluoroscopic image A61.

However, according to the present embodiment, the combination of a second candidate of the fluoroscopic image A and the first candidate of the fluoroscopic image B corresponding to having the largest F value in the table shown in FIG. 6 is detected as the marker 29.

Note that when at least one of the matching scores in the combination fluoroscopic image A 61 and the fluoroscopic image B 62 corresponding to the largest F value is not the highest matching score in the corresponding list, the detection accuracy of the marker 29 may decrease. Therefore, it may be configured to transmit a gate OFF signal even when a measured position of the marker 29 is within the gate range or to display an alert regarding the matching score along with information about the common vertical line on the console 43 to be described later.

The above-described proton beam irradiating system according to the present embodiment employs an irradiation method/irradiation technique called a spot scanning method. The spot scanning method is a method of forming a dose distribution that matches the shape of a target by arranging dose distributions formed by thin proton beams. A proton beam advances in a body while losing energy, and the energy loss is maximized immediately before stopping. The shape of a dose distribution due to the energy loss is called a Bragg curve and has a peak at the end of a range. A depth at which a proton beam forms a peak can be adjusted by changing the energy of the proton beam. Also, the shape of a dose distribution in a direction vertical to a beam axis formed by a proton beam is mostly a normal distribution. A position where a dose distribution is formed in a direction vertical to a beam axis can be adjusted by scanning a proton beam by using a scanning magnet. By combining changing of energy with a scanning unit a scanning magnet, a uniform dose distribution can be formed throughout a target.

Returning to FIG. 1, the database 42 stores parameters for irradiation that are created by a treatment planning system and the like, and the control apparatus 40 receives necessary information from the database 42 before irradiation.

The console 43 is connected to the control apparatus 40 and the moving object tracking control apparatus 41 and displays information on a display screen based on signals acquired from the control apparatus 40 and the moving object tracking control apparatus 41. Furthermore, the console 43 receives an input from an operator who operates the proton beam irradiating system and transmits various control signals to the control apparatus 40 and the moving object tracking control apparatus 41. For example, the console 43 displays a fluoroscopic image acquired by the X-ray fluoroscopic device and status of tracking the marker 29. Also, from the console 43, parameters necessary for tracking the marker 29 can be set.

FIGS. 7A and 7B show screen images for tracking a moving object related to the moving object tracking control apparatus 41 displayed on the console 43.

On the screen image of FIG. 7A, the fluoroscopic image A61 acquired by the X-ray measuring device 24A and the fluoroscopic image B62 acquired by the X-ray measuring device 24B are displayed. A fluoroscopy start button 50, a gate start button 51, a setting button 52, and a tracking lock button 53 are displayed on the left side of the fluoroscopic image A61. Furthermore, on the lower side of the fluoroscopic image B62, a result display section 54a displaying a result of comparing a matching score acquired through a template matching regarding the fluoroscopic image A61 acquired by the X-ray measuring device 24A with a first predetermined value set in advance through a color distinction and a result display section 54b displaying a result of comparing a matching score acquired through a template matching regarding the fluoroscopic image A61 acquired by the X-ray measuring device 24B with the first predetermined value set in advance through a color distinction are displayed. Here, the result display sections 54a and 54b are not limited to display color distinctions, and numerical values may be displayed as-is.

When the setting button 52 shown in FIG. 7A is pressed, the screen image shown in FIG. 7B is displayed. The screen image shown in FIG. 7B includes input sections for weights for the above-stated evaluation function, that is, a $W_A$ input section 55, a $W_B$ input unit 56, a $W_L$ the input unit 57, an input unit 58 for the lowest score $T_A$ regarding the fluoroscopic image A61 acquired by the X-ray measuring device 24A, and an input unit 59 for the lowest score $T_B$ regarding the fluoroscopic image B62 acquired by the X-ray measuring device 24B.

When the tracking lock button 53 is pressed, the moving object tracking control apparatus 41 switches between a first mode for detecting the position of a tracking target based on a value representing the accuracy of detection and a value representing a correlation and a second mode for detecting the position of a tracking target based on only the value representing the accuracy of detection.

Next, the procedure in the case of irradiating a proton beam will be described.

First, the irradiation target 26 is fixed onto the couch 27. Next, the irradiation target 26 is moved to a position planned in advance by moving the couch 27. At this time, a fluoroscopic image using an X-ray fluoroscopic device is captured so as to confirm that the irradiation target 26 is moved to the position planned in advance.

When an irradiation preparation button on the console 43 is pressed by an operator, the control apparatus 40 reads the information about a gantry angle, energy, and a spot from the database 42. In accordance with the read gantry angle, the operator presses a gantry rotation button at the console 43 to rotate the gantry 25.

After rotation of the gantry 25 is started, the operator presses the fluoroscopy start button 50 at the console 43, thereby starting an X-ray fluoroscopy with respect to the moving object tracking control apparatus 41.

After the X-ray fluoroscopy is started, the operator selects the marker 29 to be tracked on the screen image, thereby starting tracking of the marker 29 on each fluoroscopic image. A template matching is used for tracking the marker 29. In the template matching, a position that most closely matches the pattern of an image of the marker 29 registered in advance as a template image is searched for in a fluoroscopic image. As the marker 29, a position corresponding to the maximum matching score on each fluoroscopic image is detected and tracked.

After confirming the start of tracking of the marker 29 on the two fluoroscopic images corresponding to the two X-ray fluoroscopic devices, the tracking lock button 53 is pressed. After the tracking lock button 53 is pressed, the method of tracking the marker 29 executes a first mode for detecting the marker 29 using an evaluation function reflecting the matching scores and the length of the common vertical line described above. After a gate range is set and it is confirmed that the marker 29 is being tracked, the gate start button 51 is pressed. When it is determined by pressing the gate start button 51 that the position of the marker 29 is within the gate range, a gate ON signal is transmitted from the moving object tracking control apparatus 41 to the control apparatus 40. If the tracking lock button 53 is not provided, when tracking of the marker 29 is started with two fluoroscopic images, it may be automatically shifted to a method of detecting the marker 29 reflecting matching scores and the length of a common vertical line.

When the operator presses the irradiation start button on the console 43, the control apparatus 40 first accelerates a proton beam up to an initial irradiation energy based on information about energy and a spot read from the database 42.

Specifically, the control apparatus 40 controls the ion source 12 and the linac 13 to primarily accelerate a proton beam generated by the ion source 12 by linac 13 and makes the accelerated proton beam to incident on the synchrotron 11.

Next, the control apparatus 40 controls the synchrotron 11 to accelerate the incident proton beam to the initial irradiation energy. The proton beam circulating in the synchrotron 11 is accelerated by a radiofrequency from the radiofrequency acceleration system 18. The control apparatus 40 controls an excitation amount of the bending magnets 21 and the quadrupole electromagnet of the beam transport line 20, such that the proton beam having the initial irradiate energy can reach the irradiation nozzle 22 from the synchrotron 11.

The amount of excitation of the two scanning magnets in the irradiation nozzle 22 is set, such that the proton beam reaches an initial irradiation spot included in the spot information from the database 42.

After these settings are completed, if the control apparatus 40 has received a gate ON signal from the moving object tracking control apparatus 41, irradiation of the proton beam is started.

If a gate OFF signal has been received, it is waited until receiving the gate-on signal.

After receiving the gate ON signal, the control apparatus 40 applies a radiofrequency wave to the radiofrequency extractor 19 to start extraction of the proton beam. When a radiofrequency wave is applied to the radiofrequency extractor 19, a part of the proton beam circling in the synchrotron 11 passes through an extraction deflector 17, passes through the beam transport line 20, and reaches the irradiation nozzle 22. The proton beam reached the irradiation nozzle 22 is scanned by two scanning magnets, passes through a dose monitor and a position monitor, reaches a target of the irradiation target 26, and forms a dose distribution. An irradiation amount per spot is registered in the spot information from the database 42. When an irradiation amount measured by the dose monitor reaches a value registered in the spot information, the control apparatus 40 controls a radiofrequency wave for extraction and stops extraction of the proton beam. After extraction of the proton beam, the control apparatus 40 calculates an arrival position of the proton beam at the target position from the position information of the proton beam measured by the position monitor and confirms that it is consistent with a position registered in the spot information.

Since the control apparatus 40 irradiates a proton beam to a next spot, an excitation amount of scanning magnets is set so that the proton beam reaches a position registered in the spot information. After completing the setting, if a gate ON signal is continuously received, the control apparatus 40 controls the radiofrequency wave for extraction and starts extraction of the proton beam. If a gate OFF signal has been received, it is waited until receiving the gate-on signal. If a gate OFF signal is received during the irradiation to a certain spot, the extraction of a proton beam is continued until the irradiation onto the spot is completed.

When irradiation onto a spot is repeated and irradiation of spots to be irradiated with the initial energy is completed, the control apparatus 40 controls the synchrotron 11 to decelerate the proton beam and starts preparation for irradiation of a proton beam having a next energy. Like in the case of the initial energy, the control apparatus 40 controls the ion source 12 and the linac 13 to make a proton beam incident on the synchrotron 11 and controls the synchrotron 11 to accelerate the proton beam up to a second energy. The control apparatus 40 controls the beam transport line 20 and the scanning magnets and continues irradiation onto a spot.

By repeating the above operations, proton beams are irradiated onto all spots read from database 42. When irradiation is completed, an irradiation completion signal is transmitted from the control apparatus 40 to the moving object tracking control system 41. When the irradiation completion signal is received, the moving object tracking control apparatus 41 controls the fluoroscopic X-ray generators 23A and 23B to stop X-ray fluoroscopy.

In the case of irradiating proton beams onto the target in a plurality of directions, after changing the angle of the gantry 25 and the position of the couch 27, the operator presses the irradiation preparation button and repeats irradiation of proton beams in the same manner.

Next, effects of the present embodiment will be described.

In the radiation irradiating system and the moving object tracking system according to the above embodiments of the present invention described above, a template matching is performed on two fluoroscopic images by using a template image representing the marker 29 prepared in advance, and positions corresponding to high matching scores are listed as candidates of the position of the marker 29. From two lists of the candidates of the position of the marker 29, the lengths of common vertical lines for all combinations are calculated. Then, the position of the marker 29 is detected based on the matching score and the common vertical line. Then, based on the detected position of the marker 29, an amount of a proton beam to be irradiated to a target is controlled.

Accordingly, even when an X-ray photographing condition is severe due to circumstances like the thick irradiation target 26, the moving object tracking system 38 can track the marker 29. Therefore, by reducing the frequency of losing track of the marker 29, it is possible to omit the trouble for an operator to instruct the moving object tracking system to redetect the marker 29 with high accuracy when the operator loses track of the marker 29, and thus an irradiation time can be shortened. In addition, by shortening the irradiation time, the number of times of X-ray fluoroscopy can be reduced, and thus the exposure dose of the irradiation target 26 can also be reduced. Furthermore, since the marker 29 can be tracked even when the quality of a fluoroscopic image is degraded, the marker 29 can be tracked even if the intensity of an X-ray in the X-ray fluoroscopic device is reduced, and thus the exposure dose of the irradiation target 26 can also be reduced.

Also, the value representing the correlation is the length of the common vertical line corresponding to the shorted distance between the positions on the X-ray measuring devices 24A and 24B corresponding to the positions of the candidates on the fluoroscopic image A61 and the fluoroscopic image B62 and the X-ray generating devices 23A and 23B. As described above, erroneous detection of a tracking target occurs as the length of a common vertical line increases. Therefore, by using the length of the common perpendicular as the value representing the correlation, the detection accuracy of the marker 29 can be improved, and thus the frequency of erroneous detections can be reduced.

Furthermore, the moving object tracking control apparatus 41 and the control apparatus 40 can improve irradiation accuracy of a proton beam to a target by irradiating the proton beam when the position of the marker 29 is within a range specified in advance.

Also, the moving object tracking control apparatus 41 can be switched between a first mode for detecting a position of the marker 29 based on the value representing the accuracy of the detection and the value representing the correlation and a second mode for detecting a position of the marker 29 based on only the value representing the accuracy of the detection, and thus the marker 29 can be tracked according to irradiation conditions, e.g., a status of the irradiation target 26.

Furthermore, the moving object tracking control apparatus 41 may compare the matching score with a first predetermined value and outputs a result of the comparison to the console 43. Therefore, a state in which a matching score is low, that is, the marker 29 is lost can be promptly confirmed on the console 43, and thus the marker 29 can be re-detected promptly. Therefore, it is possible to more reliably suppress the prolongation of an irradiation time, and thus the irradiation time can be further shortened.

In addition, the moving object tracking control apparatus 41 can apply weights to matching scores and common vertical lines and detect the position of the marker 29 based on the weight application. Therefore, even when X-ray imaging conditions are severe, the position of the marker 29 can be detected more accurately and the irradiation time can be shortened.

Furthermore, when determining that a value representing the accuracy of a detection, if it is determined that a same candidate is selected, the moving object tracking control apparatus 41 sets a position corresponding to the optimal value indicating the accuracy of the detection as the position of the candidate of the marker 29. Therefore, unnecessary selection of positions of candidates of the marker 29 can be suppressed, and thus the overall time elapsed for detecting the position of the marker 29 can be reduced. Therefore, it contributes to reduction of the irradiation time.

Furthermore, if at least one of the matching scores of the fluoroscopic image A61 and the fluoroscopic image B62 in a combination corresponding to the maximum F is not the highest value in each list, the moving object tracking control apparatus irradiation accuracy of a proton beam to a target by transmitting a gate OFF signal to be transmitted even when the position of the marker 29 is within the gate range.

In the moving object tracking control apparatus 41, furthermore, when at least one of the matching scores of the fluoroscopic image A61 and the fluoroscopic image B62 in a combination corresponding to the maximum F is not the highest value in each list, by displaying an alert regarding the matching scores on the console 43, a possibility that the marker 29 has been lost can be quickly checked on the console 43, the marker 29 can be promptly re-detected.

Furthermore, by displaying the length of a common vertical line as the information indicating the correlation of positions on the console 43, an operator can confirm information closely related to an erroneous detection of a tracking target, and thus, even if a condition for an X-ray fluoroscopy is severe (e.g., a thick target object), the operator can easily determine whether a tracking target can be accurately detected. Therefore, for example, the state in which the marker 29 is lost can be promptly confirmed on the console 43, and thus the marker 29 can be promptly re-detected. Therefore, the prolongation of the irradiation time can be suppressed, and thus the irradiation time can be shortened.

It is to be noted that the present invention is not limited to the above embodiment, and various modifications and applications are possible. The above-described embodiments have been described in detail in order to explain the present invention in an easy-to-understand manner, and are not necessarily limited to those having all the configurations described.

For example, a case in which weights are applied to the matching score and the common vertical line and the position of the marker 29 is detected based on the result of this weight application has been described. However, in the fluoroscopic image A61 and the fluoroscopic image B62, a plurality of common vertical lines can be acquired when a plurality of positions of candidates corresponding to the matching scores higher than a predetermined value can be acquired. Here, the moving object tracking control apparatus 41 can be configured to detect the position of a candidate corresponding to the highest matching score from among the plurality of common vertical lines as the position of the marker 29. Even with such a configuration, the frequency of losing track of the marker 29 is reduced, and thus the irradiation time can be shortened. In this case, the shortest maximum length of the common vertical lines during tracking for several seconds can be selected as the marker 29, for example. Furthermore, in such a case, a candidate corresponding to a short common vertical line and a high matching score can be selected as the marker 29. Furthermore, if the operator fails to track the intended marker 29 confirmed on in a screen image, the operator can also modify.

In addition, a method of starting tracking of the marker 29 has been described based on examples in which a template matching is performed with respect to each image. Alternatively, the operator can specify the position of the marker 29 on one screen image, the position of the marker 29 on the other screen image can be automatically recognized, and then a method of detecting the marker 29 reflecting matching scores and the length of the common vertical line can be automatically started.

In this case, when the position of the marker 29 is specified on one fluoroscopic images A61, a template matching is performed on a line formed by projecting a line connecting positions on the X-ray generator 23B and the X-ray measuring instrument 24B clicked by the operator onto the fluoroscopic image B62. A range in which the template matching is performed is a band-like region centered on the projected line. A plurality of candidates are extracted through a template matching in the band-shaped region, the plurality of candidates are tracked for several seconds, and the position of the marker 29 is continuously detected by using the evaluation function F.

Furthermore, although the length of the common vertical line is used as a value representing the correlation, other lengths may be used instead of that of the common vertical line.

For example, as shown in FIG. 8, it is assumed that a fluoroscopic image A and a fluoroscopic image B are images on axes perpendicular to each other and the fluoroscopic image A projects the xy plane and the fluoroscopic image B projects the xz plane. In FIG. 8, a dotted line 28A represents a straight line passing through the isocenter 31 from the fluoroscopic X-ray generator 23A, and a dotted line 28B represents a straight line passing through the isocenter 31 from the fluoroscopic X-ray generator 23B. At this time, the dotted line 28A connecting the position of the X-ray measuring device 24A and the fluoroscopic X-ray generator 23A is orthogonal to the dotted line 28B connecting the positions of the X-ray measuring device 24B and the fluoroscopic X-ray generator 23B. In this case, the x axis is common. Therefore, the x coordinates of the marker 29 acquired as a result of the template matching are ideally consistent with one another. However, in practice, deviation may occur. A difference between the x coordinates acquired from the images A and B can be used instead of the length of the common vertical line. The x axis at this time is referred to as a common axis, and a difference between values in the x axes is referred to the length of a common axis. Even when the length of the common axis is used as a value representing the correlation, the frequency of losing track of the marker 29 can be reduced.

Furthermore, even when the two fluoroscopic images are not in an orthogonal relationship, a straight line parallel to the two images can be acquired. In this case, by using the straight line as a common axis, a difference along the common axis can be used instead of the length of a common vertical line.

In the above-described embodiment, a case in which a gate irradiation is performed based on the position of the spherical marker 29 has been described. However, the marker 29 may also have a coil-like shape. In addition, although a case where the tracking target is the marker 29 has been described, the tracking target is not limited to the marker 29, and may be directly detected without using the marker 29. Alternatively, the tracking object can be a high density region within the irradiation target 26, e.g., a bone like a rib.

In addition, the irradiation method/irradiation technique may be a tracking irradiation technique for tracking irradiation points based on the position of the marker 29 or the like instead of a gate irradiation technique. For example, during a tracking irradiation of an X-ray, the orientation of an X-ray generator for forming a distribution is changed in accordance with the movement of a target, and the irradiation point of an X-ray is changed according to the movement of the target. Even in the case of a particle beam, a tracking irradiation can be performed by adjusting an excitation amount of scanning magnets according to the position of a target.

Furthermore, in the above embodiment, a case of tracking one marker 29 has been described, but the number of the markers 29 to be tracked may be plural. By tracking a plurality of markers 29, information about rotation and deformation of a target can be acquired in addition to the position information of the target. A gate irradiation or a tracking irradiation can be performed based on the information about rotation and deformation.

Conventionally, in case of tracking the plurality of markers 29, when the plurality of markers 29 temporarily overlap each other and are captured in a fluoroscopic image, it is not possible to distinguish two markers 29 when they are separated from each other. However, in another fluoroscopic image where the markers 29 do not overlap each other, the two markers 29 are separated from each other, and thus, by applying the tracking control of the present invention, it is possible to correctly distinguish the two markers 29.

In addition, it is sometimes difficult to detect the marker 29 only in one of two fluoroscopic images. In such a case, in a fluoroscopic image from which the marker 29 can be easily detected, only a candidate corresponding to the highest matching score is tracked as in the related art and candidates of the marker 29 are listed for a fluoroscopic image from which it is difficult to detect the marker 29, and thus the marker 29 can be detected from the matching scores and the lengths of common perspective lines. By determining only one candidate of marker 29 regarding one fluoroscopic image, it is possible to reduce an erroneous detection within a short calculation time.

Although an X-ray for fluoroscopy is a type of radiation, since it is not used for the purpose of forming a dose distribution, a radiation for forming a distribution is used as a generic name for radiations other than an X-ray for fluoroscopy.

Furthermore, in the above-described embodiment, the proton beam irradiating system has been described as an example. However, a radiation irradiating system of the present invention can irradiate particle beams other than a proton beam (e.g., a carbon beam), an X-ray, an electron beam, etc.

Furthermore, in the case of a particle beam irradiating device, in addition to the spot scanning method described in the above embodiment, a raster scanning method or a line scanning method for irradiating a thin particle beam without interrupting a particle beam are also applicable. In addition to the scanning method, the present invention can also be applied to an irradiation method/irradiation technique that spreads a particle beam distribution and then forms a dose distribution that conforms to the shape of a target by using a collimator or bolus, e.g., a wobbler method or a double scatter method.

In the particle beam irradiating system, cyclotron may be used in addition to the synchrotron 11 described in the above embodiment for a particle beam generator.

REFERENCE SIGNS LIST

10: proton beam generator (radiation generator)
11: synchrotron
12: ion source
13: linac
14: bending magnet
17: extraction deflector
18: radiofrequency acceleration system
19: radiofrequency extractor
20: beam transport line
21: bending magnet
22: irradiation nozzle
23A: X-ray generator
23B: X-ray generator
24A: X-ray measuring device
24B: X-ray measuring device
25: gantry
26: irradiation target
27: couch
28A, 28B: dotted line
29: marker
30: common vertical line
31: isocenter
38: moving object tracking system
39: control unit
40: control apparatus
41: moving object tracking control apparatus
42: database
43: console
50: fluoroscopy start button
51: gate start button
52: setting button
53: tracking lock button
54a: result display section
54b: result display section
55: $W_A$ input section
56: $W_B$ input section
57: $W_L$ input section
58: $T_A$ input section
59: $T_B$ input section
61: fluoroscopic image A
62: fluoroscopic image B
63: search range A
64: search range B

The invention claimed is:

1. A radiation irradiating system comprising:
a radiation irradiating device configured to generate a radiation; and
two or more pairs of X-ray fluoroscopic devices including a first X-ray fluoroscopic device and a second X-ray fluoroscopic device and configured to capture fluoroscopic images of a tracking target, each pair including one X-ray measuring device and one X-ray generator;
wherein the radiation irradiating device is controlled to detect a position of the tracking target from a first fluoroscopic image captured by the first X-ray fluoroscopic device and a second fluoroscopic image captured by the second X-ray fluoroscopic device,
wherein values indicating an accuracy of detection of a plurality of candidates of a position of the tracking target from each of the first and second fluoroscopic images and values representing a correlation between the positions of the candidates in the first fluoroscopic image and the positions of the candidates in the second fluoroscopic image are calculated, wherein calculations are performed for a plurality of pairs of candidates from the first and second fluoroscopic images by applying weights to the values indicating the accuracy of detection of each candidate and to the values representing the correlation between the positions of the candidates to generate a plurality of results, wherein a pair of candidates is selected from the plurality of pairs of candidates based on the plurality of results and the position of the tracking target is detected from the selected pair of candidates, and the radiation is controlled to be irradiated onto the target based on the detected position of the tracking target, and
wherein each of the values representing the correlation is a length of a common vertical line that corresponds to the shortest distance between at least two lines that do not intersect each other and that are connecting the positions on the X-ray measuring devices corresponding to the position of the plurality of candidates on the first and second fluoroscopic images to the X-ray generators.

2. The radiation irradiating system of claim 1, wherein the tracking target is any one of a marker for identifying the target, the target itself, and a high-density region.

3. The radiation irradiating system of claim 1, wherein the radiation irradiating device is controlled to irradiate the radiation when the position of the tracking target is within a range specified in advance.

4. The radiation irradiating system of claim 1, wherein the radiation irradiating device is controlled to be switchable between a first mode for detecting a position of the tracking target based on the values representing the accuracy of the detection and the values representing the correlation; and a second mode for detecting a position of the tracking target based on only the values representing the accuracy of the detection.

5. The radiation irradiating system of claim 1, wherein the radiation irradiating device is controlled to compare values representing the accuracy of detection with a first predetermined value and outputs the comparison result to a display unit.

6. The radiation irradiating system of claim 1, wherein the radiation irradiating device is controlled to not irradiate the radiation when a position corresponding to an optimal value representing the accuracy of the detection is not selected as a result of the weight application.

7. The radiation irradiating system of claim 1, wherein when a position corresponding to an optimal value representing the accuracy of the detection is not selected as a result of the weight application, the radiation irradiating device is controlled to output an alert signal for warning regarding the values representing the accuracy of the detection on a display unit.

8. The radiation irradiating system of claim 1, wherein the radiation irradiating device is controlled to set the position corresponding to an optimal value representing the accuracy of the detection as the position of the candidate of the tracking target.

9. A radiation irradiating system comprising:
a radiation irradiating device configured to generate a radiation; and two or more pairs of X-ray fluoroscopic devices including a first X-ray fluoroscopic device and a second X-ray fluoroscopic device and configured to capture fluoroscopic images of a tracking target, each pair including one X-ray measuring device and one X-ray generator;
wherein the radiation irradiating device is controlled to detect a position of the tracking target from a first fluoroscopic image captured by the first X-ray fluoroscopic device and a second fluoroscopic image captured by the second X-ray fluoroscopic device,
wherein values indicating an accuracy of detection of a plurality of candidates of a position of the tracking target from each of the first and second fluoroscopic images and values representing a correlation between the positions of the candidates in the first fluoroscopic image and the positions of the candidates in the second fluoroscopic image are calculated, wherein calculations are performed for a plurality of pairs of candidates from the first and second fluoroscopic images by applying weights to the values indicating the accuracy of detection of each candidate and to the values representing the correlation between the positions of the candidates to generate a plurality of results, wherein a pair of candidates is selected from the plurality of pairs of candidates based on the plurality of results and the position of the tracking target is detected from the selected pair of candidates, and the radiation is controlled to be irradiated onto the target based on the detected position of the tracking target, and
wherein each of the values representing the correlation is a distance between two or more lines that do not intersect each other and that are connecting the positions on the X-ray measuring devices corresponding to the positions of the plurality of candidates on the first and second fluoroscopic images and the X-ray generators, the distance being on a common axis.

10. A moving object tracking system comprising:
two or more pairs of X-ray fluoroscopic devices including a first X-ray fluoroscopic device and a second X-ray fluoroscopic device and configured to capture fluoroscopic images of a tracking target, each pair including one X-ray measuring device and one X-ray generator,
wherein the moving object tracking system is configured to detect a position of the tracking target from a first fluoroscopic image photographed by the first X-ray fluoroscope device and a second fluoroscopic image photographed by the second X-ray fluoroscopic device, wherein
the moving object tracking system is configured to acquire a value representing an accuracy of detection of a candidate for the position of the tracking target from each of the first and second fluoroscopic images and values representing a correlation of the positions of the plurality of candidates in the first fluoroscopic image and the positions of the plurality of candidates in the second fluoroscopic image respectively acquired by the two or more X-ray fluoroscopic devices, wherein calculations are performed for a plurality of pairs of candidates from the first and second fluoroscopic images by applying weights to the values indicating the accuracy of detection of each candidate and to the values representing the correlation between the positions of the candidates to generate a plurality of results, wherein a pair of candidates is selected from the plurality of pairs of candidates based on the plurality of results and the position of the tracking target is detected from the selected pair of candidates,
wherein each of the values representing the correlation is a length of a common vertical line that corresponds to the shortest distance between at least two lines that do not intersect each other and that are connecting the positions on the X-ray measuring devices corresponding to the position of the plurality of candidates on the first and second fluoroscopic images to the X-ray generators.

* * * * *